(12) United States Patent
Haider et al.

(10) Patent No.: US 7,685,001 B2
(45) Date of Patent: Mar. 23, 2010

(54) METHOD AND SYSTEM TO OFFER AND TO ACQUIRE CLINICAL KNOWLEDGE USING A CENTRALIZED KNOWLEDGE SERVER

(75) Inventors: Sultan Haider, Erlangen (DE); Volker Wetekam, Rathsberg (DE)

(73) Assignee: Siemens Aktiengesellschaft, Munich (DE)

( * ) Notice: Subject to any disclaimer, the term of this patent is extended or adjusted under 35 U.S.C. 154(b) by 1133 days.

(21) Appl. No.: 11/302,852

(22) Filed: Dec. 14, 2005

(65) Prior Publication Data
US 2007/0179804 A1    Aug. 2, 2007

(51) Int. Cl.
*G06Q 10/00* (2006.01)
*G06Q 50/00* (2006.01)
*A61B 5/00* (2006.01)
*G06F 19/00* (2006.01)

(52) U.S. Cl. .............................. 705/2; 705/3
(58) Field of Classification Search ............ 705/2, 705/3; 600/300
See application file for complete search history.

(56) References Cited

U.S. PATENT DOCUMENTS

| 6,458,080 B1* | 10/2002 | Brown et al. ............... 600/300 |
| 6,482,156 B2* | 11/2002 | Iliff ........................... 600/300 |
| 6,687,685 B1* | 2/2004 | Sadeghi et al. .............. 706/15 |
| 2003/0092980 A1 | 5/2003 | Nitz | |

* cited by examiner

*Primary Examiner*—Gerald J. O'Connor
*Assistant Examiner*—Neha Patel
(74) *Attorney, Agent, or Firm*—Schiff Hardin LLP

(57) ABSTRACT

In a method and system for providing clinical knowledge from a provider to a medical user based on one or more diagnostic questions submitted by the user to the provider, a clinical knowledge communication server is provided with an associated knowledge database. The at least one or more diagnostic questions are sent by the user to the server. With the server, an initial examination of the at least one or more diagnostic questions is conducted. Examination steps are associated with the at least one or more diagnostic questions and placed in a sequence. The sequence of examination steps are then sent to the medical user. The provider may also request clinical knowledge from the medical user such as, for example, relating to the diagnostic questions submitted by the user.

24 Claims, 4 Drawing Sheets

EXAMPLE OF AN EXAMINATION STEP

| | ANSWER DIAGNOSTIC QUESTIONS 1, 3 ... |
|---|---|
| | SEQUENCE ATTRIBUTE |
| EXAMINATION STEP A | EXAMINATION DURATION ATTRIBUTE |
| | SELECT ATTRIBUTE |
| | ... ATTRIBUTE |

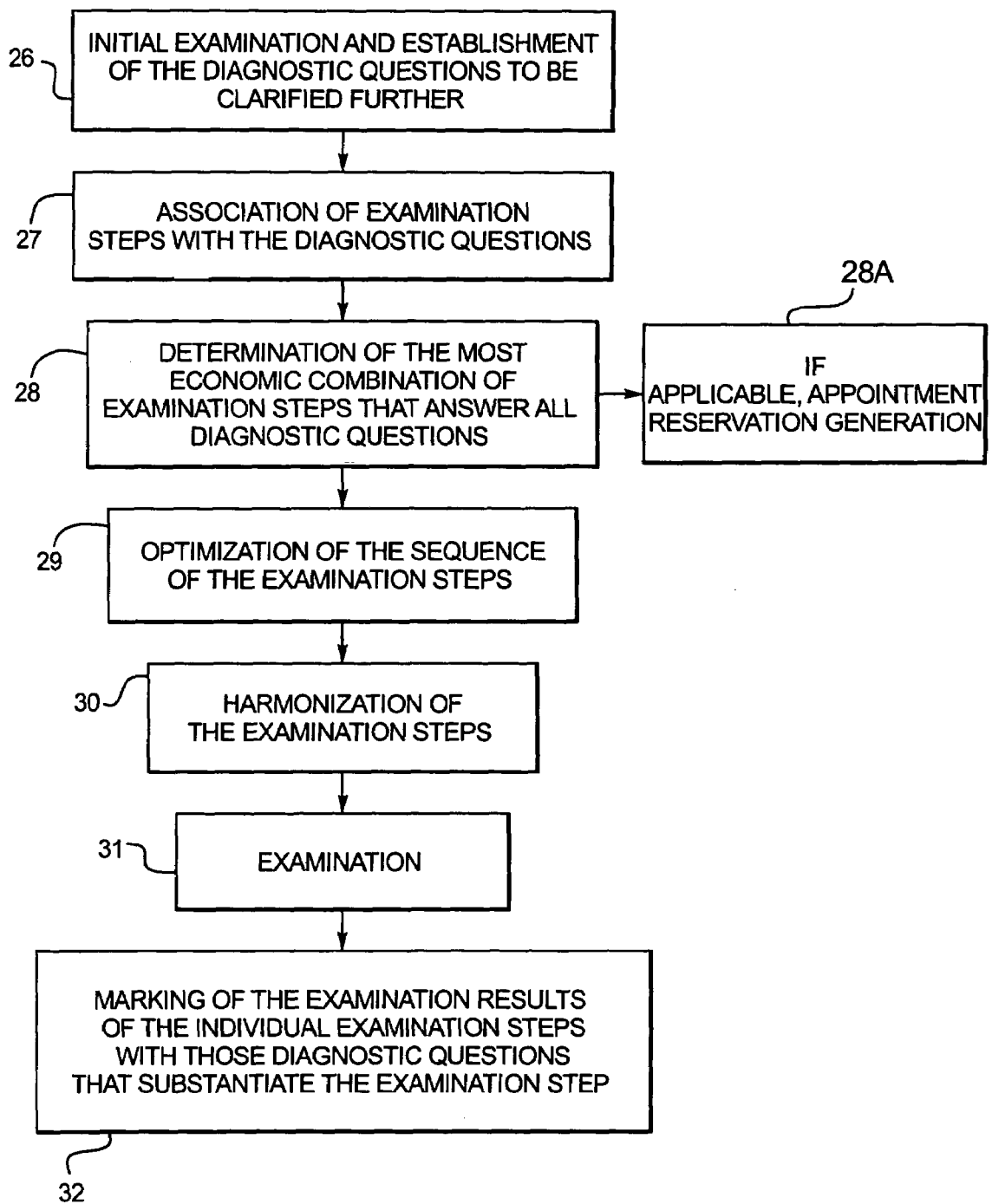

METHOD AND SYSTEM TO OFFER AND TO ACQUIRE CLINICAL KNOWLEDGE USING A CENTRALIZED KNOWLEDGE SERVER

BACKGROUND

In the prior art clinical scenario, a patient diagnosis/therapy is dependent on resources available in the clinical facility. However, given the growing complexity and costs of imaging devices such as Magnetic Resonance Imaging (MRI), Computed Tomography (CT), Nuclear Medicine (NM), and Ultrasound (US), a lot of experience and clinical expertise are needed to make optimum use of the potential of these imaging devices, e.g. how a patient suffering from Acute Cerebral Insult has to be treated within a clinical facility, what is the sequence of examination at CT, US, and Magnetic Resonance (MR) devices, which examination protocols are to be used, which post processing application/tools are to be used etc.

Due to research and/or business focus of the clinical facility in many cases certain special sequences, protocols, post processing applications, etc. are rarely used, and the cost of having them all is very high. Also, it is difficult to maintain updates of the developments taking place (e.g. what are best protocols, sequences for treating a patient with prostate cancer).

MR, for example, being a non-invasive modality, offers a variety of image contrasts through numerous techniques. During the last decades, rapid technological advancements in the area of new applications, sequences, hardware, post-processing, therapies based on results, etc. pose challenges to the MR scientific community (Radiologists and MR Manufacturers) to maintain updated knowledge about best possible clinical applications. However, such clinical expert knowledge would be useful to streamline workflow and optimize the use of MR innovative applications.

Medical care providers issue increasingly clear process documents for their medical and diagnostic capacities. The examination indication is linked, conditional upon the patient and the disease, with very specific questions that are to be answered by the examination.

Complex examination methods (modalities) allow the examiner an adaptation of the examination flow path (for example measurement protocol in Magnetic Resonance Tomography (MRT)) to the question to be answered. The complexity can pertain both to the "measurement" itself and to possibly necessary post-processing and document steps. Complex examination methods are, for example, MRT, CT, and laboratory diagnostics.

The association of a medical question with a commensurate examination flow path can be difficult and at the same time require deep understanding of the examination methods and of the diseases to be examined. However, the examination is often conducted by personnel who do not possess the qualification to adapt the examination flow path to the question.

The same problem also arises one level higher, where it is imperative to select the diagnostic procedures and modalities commensurate with the medical question.

In the prior art, standardized examination protocols are pre-defined at the examination apparatus. The examiner makes a selection under the standard protocols corresponding to the question. The standard protocols are, if applicable, still adapted by expensive, highly-qualified personnel.

However, in many cases this procedure leads to unsatisfactory results. For example, the medical questions are many-sided and can often not be directly associated with one standard protocol. The user then selects one or more standard protocols that, however, in summation incorporate the answer to the question, but however, often also exceed it. The examination is thus more extensive (more expensive) than is necessary.

Both the number of the medical questions that are addressed at one modality and the number of the possible examination flow paths (for example in MRT: questions from all organ regions and very many diseases—typically >1000 standard protocols) can be very large. In these cases, medical expertise is already necessary in order to associate a standardized examination flow path with a medical question.

Moreover, combinations of questions are always provided for which an optimal standard protocol cannot be defined in advance.

The selection of the commensurate procedure and modality is often regulated internal to a department at the higher levels.

The rules are in part fixed in writing, however are also in part only present as an oral consensus between the participating doctors.

SUMMARY

In a method and system for providing clinical knowledge from a provider to a medical user based on one or more diagnostic questions submitted by the user to the provider, a clinical knowledge communication server is provided with an associated knowledge database. The at least one or more diagnostic questions are sent by the user to the server. With the server, an initial examination of the at least one or more diagnostic questions is conducted. Examination steps are associated with the at least one or more diagnostic questions and placed in a sequence. The sequence of examination steps are then sent to the medical user.

The provider may also request clinical knowledge from the medical user such as, for example, relating to the diagnostic questions submitted by the user.

BRIEF DESCRIPTION OF THE DRAWINGS

FIG. 3 is a block diagram showing steps in automatic generation of a complex medical examination path on the basis of diagnostic questions;

DESCRIPTION OF THE PREFERRED EMBODIMENT

Figure 1:
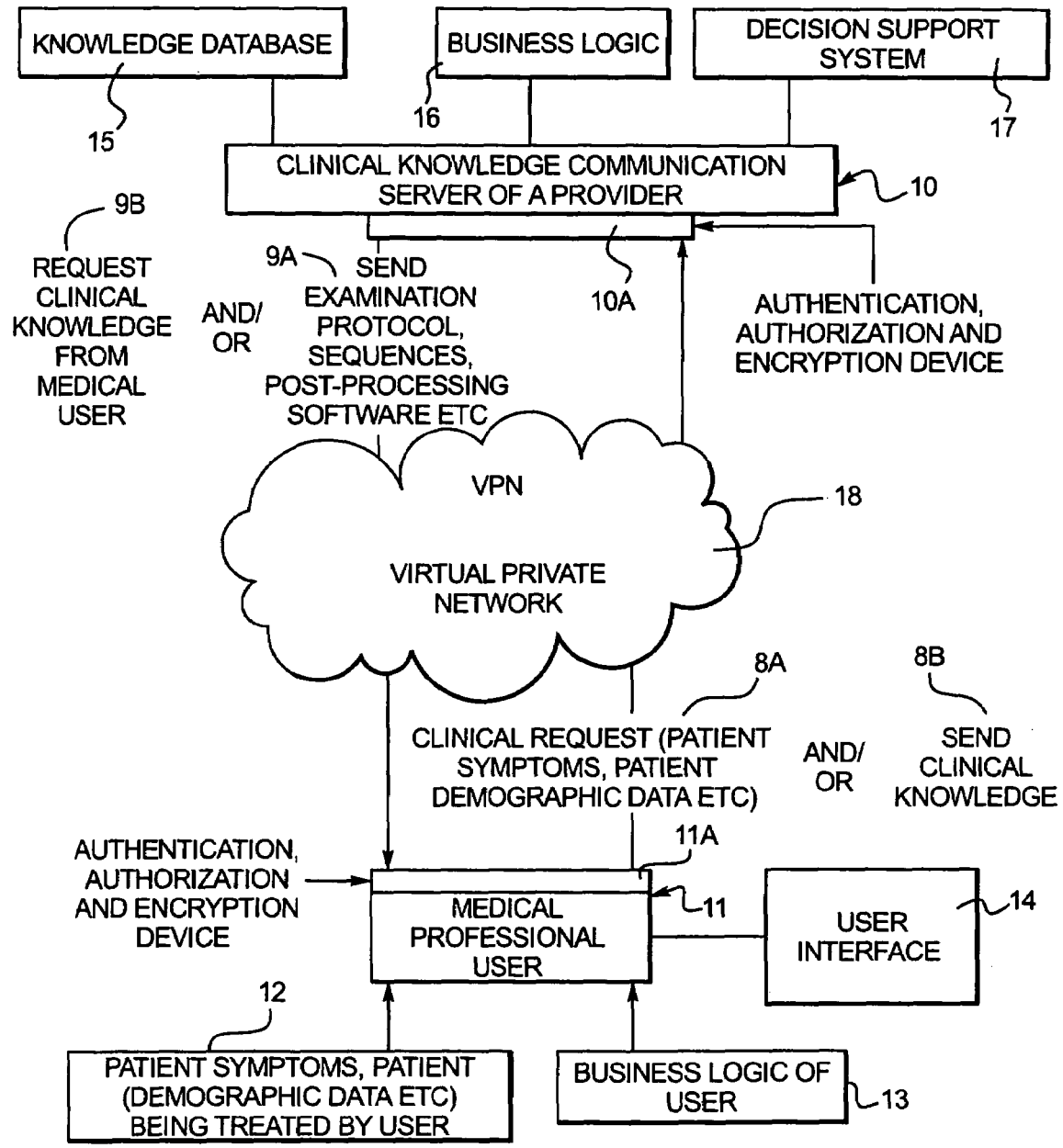
FIG. 1 is a block diagram of a method and system to offer clinical knowledge to a medical user using a centralized knowledge server of a provider, and/or to acquire related clinical knowledge from the medical user.

For the purposes of promoting an understanding of the principles of the invention, reference will now be made to the preferred embodiment illustrated in the drawings and specific language will be used to describe the same. It will nevertheless be understood that no limitation of the scope of the invention is thereby intended, such alterations and further modifications in the illustrated device, and/or method, and such further applications of the principles of the invention as illustrated therein being contemplated as would normally occur now or in the future to one skilled in the art to which the invention relates.

The system and method comprises, as shown in FIG. 1, a centralized clinical knowledge communication server 10 of a provider. The provider may, for example, be a company which specializes in providing medical imaging equipment for patient examination such as magnetic resonance imaging (MRI), computer tomography (CT), nuclear magnetic imaging (NM), Ultrasound (US) etc. One or more medical professional users 11 send, via an authentication, authorization, and encryption device 11A, a clinical request 8A comprised of, for example, patient symptoms along with patient demographic data 12. At the provider level, a knowledge data base 15 is provided comprising various databases e.g. an atlas for various clinical protocols for various imaging devices, sequences, and a rule database. A decision support system 17 and business logic 16 are also provided. At the user level there is also a user interface 14 and a business logic 13 of the user.

Figures 2, 4:
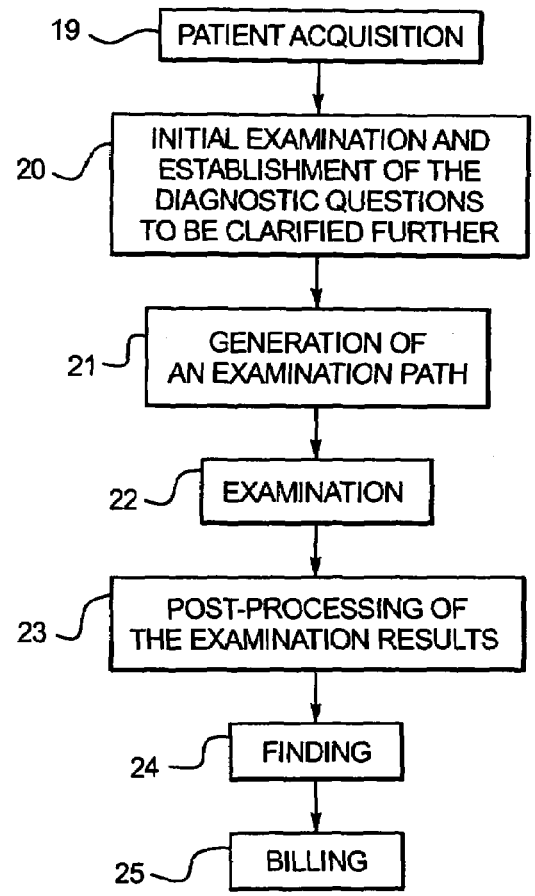
FIG. 2 is a flowchart of a workflow in prior art diagnostic examination.
FIG. 4 is a chart exemplifying an examination step.

The workflow of a typical prior art diagnostic examination by a medical professional 11 is shown in FIG. 2 by steps 19-25.

The medical professional 11 (the user) sends a clinical request 8A (diagnostic questions, patient symptoms, patient demographic data etc.) to the centralized knowledge server 10 (of the provider) via a communication protocol (TCP/IP, Bluetooth etc.) represented by the virtual private network (VPN) 18.

The server 10 analyzes the clinical request 8A using a rule engine, the decision support system 17 and the business logic 13 and determines the types of information 9A including a medical examination path in response to diagnostic questions, which the server 10 will send to the user 11. For example, these information types 9A may include the best possible examination protocols, procedures and post-processing tools needed based on the pathological findings.

The knowledge database 15 has a variety of information sources stored therein including best clinical protocols; hanging protocols; user interfaces for MRI, CT, US, NM etc.; special sequences; post-processing software; etc.

The user 11 selects the protocols (hanging protocols), post-processing software packages etc. he desires and downloads them through the local system network 18 (which can use various communication protocols such as TCP/IP, Bluetooth, etc.).

The provider may also use the clinical knowledge communication server 10 to accumulate clinical knowledge. Separately or as part of servicing the clinical request from the medical user, the server 10 of the provider may make a request 9B for clinical knowledge from the medical user 11. The medical user 11 then responds by sending clinical knowledge 8B to the provider 10. This clinical knowledge may relate to the clinical request 8A of the medical user 11, but does not necessarily have to so relate. Also, one way for the medical user 11 to pay for the information 9A which the medical user 11 is receiving in response to his diagnostic questions (clinical request) is to "trade" or "barter" the medical user's own clinical knowledge as partial or complete payment to the provider.

Stated differently, the user and the provider may auction the medical information about the diagnosis and therapeutic procedures by use of the business logic 13 of the user 11 and the business logic 16 of the provider (e.g. pay per user, free license, bonus points for usage giving access to certain forms, conferences, workshops, etc.). Considering the privacy issues, getting patient data is very sensitive in most countries. The proposed system provides a method for developing/selling clinical trends/knowledge for the patient diagnosis/therapy information. The patient/medical professional in return for his/her data receives benefit such as financial incentives, best examination methods, access to certain DNP, etc.

The user 11 thus has a possibility to buy/sell hanging protocols, post-processing tools required for/based on his/her diagnosis/therapy. This exchange of information helps in updating the knowledge data base 15 of the provider.

The business logic component 16 at the server 10 or the business logic 13 of the user thus can provide logic for these kinds of information exchange depending on the particular medical user or provider. Thus the business logic component also makes use of system utilization data. The system utilization data is collected by the provider from its customers, such as imaging equipment customers. The system utilization data is processed using data mining tools for extracting information about the best protocols/post-processing tools used for answering certain diagnostic questions. The system networks, Bayesian methods, genetic algorithms etc. for a self-learning mechanism.

The system can also suggest, for a specific case, an additional hardware/software component required in the clinical facility of the user 11 to treat the patient with certain symptoms.

The server 10 is also useful for finding a vendor for faulty components or for sending an error log file from a faulty software or hardware for evaluation for performance/quality assurance.

With the authentication, authorization, and encryption device 10A, the system can also make use of encryption for data transfer between the server 10 and the user 11. It makes use of hardware devices such as smart cards for authentication.

The server 10 can be accessed by a call center.

For automatic generation of a complex medical examination path on the basis of one or more diagnostic questions to be answered, reference is made to the method steps of FIG. 3 which are performed by the software of the clinical knowledge communication server 10, business logic 16, and decision support system 17 of the provider shown in FIG. 1.

Starting from the medical questions that lead to an examination (step 26 in FIG. 3), one or more examination steps (=individual measurement from an examination protocol) are automatically associated with each individual medical question (step 27). See FIG. 4 showing an example of an examination step associated with diagnostic questions.

In a simple case, the questions are registered in a structured manner (for example as a selection from a suggestion list) and converted into examination steps via a table. See step 27 in FIG. 3 and FIG. 4—an example of an examination step and attributes thereof derived from diagnostic questions.

Some modalities can be very flexibly adjusted and enable the answering of a question with various alternative examination steps (example: bleeding indication in the brain either in a B0 image of a diffusion measurement or with a T2*-weighted FLASH measurement). A question can also sometimes be answered by various modalities. In these cases, a question refers to a plurality of alternative examination steps. The decision as to which examination step should then actually be used for an examination is supported by attributes of the alternative examination steps (see step 28 in FIG. 3—most economic combination of examination steps). These attributes can be seen in FIGS. 4 and 5. The attributes can, for example, be a prior approval viewing (which alternative is the most advantageous . . . ) or indications as to "usage when the examination step is already taken by another question for this examination" or "can additionally be measured when it is also reasonable for other questions" or . . . etc.

Figure 5:
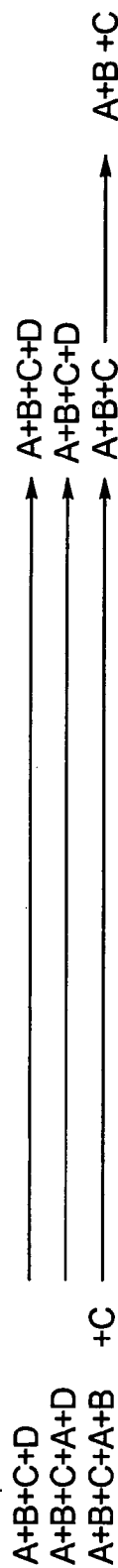
FIG. 5 is a chart showing marking of examination results with diagnostic questions.

An attribute "examination duration" is associated with each examination step (See FIGS. 4 and 5). In order to predict the duration of the examination, the examination times of the examination steps are added up and added to the modality-specific setup times and, if applicable, buffer times. A free time period at the corresponding modality can be automatically proposed or reserved with this prediction of the examination duration.

Thus the examination steps bear attributes by use of which the development of the examination path can automatically occur: the examination steps that belong to the individual questions are combined; and redundant examination steps are eliminated (step 28).

As shown at 28A in FIG. 3, if applicable, a deployment reservation may be generated.

After the examination steps have been selected to answer all provided questions, the sequence of the examination steps is optimized (step 29 in FIG. 3). For this, "sequence attributes" that are evaluated by a sorting logic are associated with the examination steps (See FIG. 4). "Sequence attributes" can, for example, be "pre-contrast", "post-contrast", "earliest 300s after contrast administration", "first examination step", after examination step x". The sorting logic evaluates the sequence and examination duration attributes and derives an optimal sequence of the examination steps (step 29).

The individual examination steps of an examination are subsequently harmonized to one another (step 30). Thus, an optimal, less complicated examination path results for the examination (step 31) that answers all diagnostic questions. For example MR: equal volume coverage (field of view and slab thickness) for measurements with the same orientation.

When a plurality of questions are answered in the framework of an examination, the examination path (step 31 in FIG. 3) sent to the user 11 Is comprised of the sum of the examination steps that were associated with the individual questions from the user 11, whereby a plurality of individual examination steps are only undertaken once (i.e. the examination is comprised of the smallest superset of the identified examination steps for all user questions).

Information about the "question relevance" is given with the result or results of the examination (often, for example, an image series). This information allows the data (for example in a PACS) to be organized for the purposes of the data navigation, the correct images to be selected for the post processing and, if applicable, to be automatically loaded in the correct applications, and enables the correct data to be offered for the finding (sorted according to the answered question).

Marking of these examination results of the individual examination steps with those diagnostic questions that substantiate the examination step is undertaken as shown in step 32 of FIG. 3. This concept can be extended to the entire diagnostic.

In addition to the association of examination steps to a medical diagnostic question (step 27), the required modality can be automatically selected. An automated suggestion as to which sequence the patient should be examined at which modalities can then be automatically given based on the steps that are necessary overall. A connection with an automated date definition may also be performed.

Marketing benefits of the disclosed system and method for a provider who is, for example, an imaging device provider, are:

the provider provides ASP-based knowledge for optimizing workflow sequences along with standardization of imaging routines (e.g. best practice hanging protocols for various diseases);

additional licensing fee for special options;

the provider will be marketing for the entire hospital workflow—it can be suggested to the customer to make use of provider equipment by showing the benefits Impact on the brand value of provider;

additional market growth;

the provider can foresee markets for new software/hardware applications;

the provider can provide consultancy to Pharmacy-companies for clinical trails and can generate new business models;

software development: protocol optimization, evaluation of WIPs, clinically acceptable image quality definition, HIS/RIS network planning, evaluation of diagnostic procedures, development of new sequences, etc. can be made;

based on customer workflow new hardware applications can be developed e.g. if 5% better homogeneity in the MR magnet results in 15% better customer workflow, considering the cost of development and profit margin a decision can be made;

the provider can foresee the defects in the servicing hardware/software and can advise the user for a patient scheduling;

the provider can do best practice sharing;

remote scanning can be made and remote diagnosis can be provided—additional consultancy fee.

The provider can influence healthcare policies by providing consultancy and solutions to Health care ministries of various countries and can play a significant role in global healthcare.

The provider can make benchmarking with government organizations for planning costs and providing an insight about current/future diseases.

User-Customer Benefits are:

highest throughout;

reduced workforce (e.g. less persons required for scheduling;

cost reduction;

better and faster servicing;

higher up-time for the system.

Patient benefits are:

shortest time for diagnostic

While a preferred embodiment has been illustrated and described in detail in the drawings and foregoing description, the same is to be considered as illustrative and not restrictive in character, it being understood that only the preferred embodiment has been shown and described and that all changes and modifications that come within the spirit of the invention both now or in the future are desired to be protected.

We claim as our invention:

1. A method for providing clinical knowledge from a provider to a medical user, comprising the steps of:
providing a clinical knowledge communication server with an associated knowledge data base of said provider;
said user having a user interface for communicating with said communication server of said provider;

providing an authentication, authorization, and encryption device associated with said user interface and providing an authentication, authorization, and encryption device associated with said communication server;

said user obtaining patient symptoms for a specific patient;

said user creating a plurality of diagnostic questions based on said patient symptoms representing a plurality of potential diagnoses for a medical problem causing said symptoms in said patient;

said user sending said plurality of diagnostic questions along with said patient symptoms to said server;

with the server conducting an initial examination of the plurality of diagnostic questions and patient symptoms;

with the server associating for each of the diagnostic questions a corresponding set of examination steps to create a corresponding sequence of examination steps for each of the diagnostic questions, at least one of said sequences comprising use of a medical imaging machine, and providing a respective examination protocol for said imaging machine including sequences, and a post-processing software for use with an image created by said imaging machine; and encrypting and then sending said sequence of examination steps for each of said diagnostic questions to said medical user interface where they are decrypted.

2. A method of claim 1 wherein after the step of associating the examination steps, said server:

determines an economic combination of the examination steps that answer said diagnostic questions;

optimizes a sequence of the examination steps; and sends said optimized sequence of examination steps to said medical user.

3. A method of claim 2 wherein attributes are generated for association of examination steps with said at least one or more diagnostic questions, and said attributes are used for determining said economic combination of the examination steps that answer said diagnostic questions.

4. A method of claim 2 including the further step of after optimizing the sequence of the examination steps, said server harmonizes the examination steps.

5. A method of claim 1 wherein a marking is performed of examination results of the individual examination steps with the diagnostic questions that substantiate the examination step.

6. A method of claim 1 including the step of providing a business logic of said medical user to said clinical knowledge server for determining kinds of information exchange between said user and said provider.

7. A method of claim 6 wherein said business logic of the user is sent to the server at the time that the diagnostic questions are sent.

8. A method of claim 1 wherein in addition to the patient symptoms, the user also sends patient demographic data.

9. A method of claim 1 wherein the clinical knowledge server has a business logic component associated therewith.

10. A method of claim 9 wherein said business logic component performs a step of making use of system utilization data from customers of the provider.

11. A method of claim 10 wherein the clinical knowledge server also has a decision support system associated therewith, and the server processes the system utilization data for extracting information about best protocols or best processing tools used for answering certain of said diagnostic questions.

12. A method of claim 1 wherein said provider requests clinical knowledge from said medical user and said medical user sends clinical knowledge to said provider based on said request from said provider.

13. A method of claim 12 wherein said clinical knowledge sent by said medical user relates to said diagnostic questions from said user.

14. A method of claim 12 wherein a business logic of said provider associated with said clinical knowledge communication server contains information for exchange of clinical knowledge for particular medical users.

15. A system for providing clinical knowledge from a provider to a medical user, comprising:

a clinical knowledge communication server with an associated knowledge data base of said provider;

a user interface of said user for communicating with said communication server of said provider;

an authentication, authorization, and encryption device associated with said user interface and an authentication, authorization, and encryption device associated with said communication server;

said user interface sending to said server symptoms for a specific patient and a plurality of alternative diagnostic questions based on said patient symptoms representing a plurality of potential alternative diagnoses for a medical problem causing said symptoms in said patient;

said server conducting an initial examination of the plurality of diagnostic questions and patient symptoms;

said server associating for each of the diagnostic questions a corresponding set of examination steps to create a corresponding sequence of examination steps for each of the diagnostic questions, at least one of said sequences comprising use of a medical imaging machine and a respective examination protocol for said imaging machine including sequences, and a post-processing software for use with an image created by said imaging machine; and said encryption device associated with said server encrypting, and said server sending, said sequence of examination steps for each of said diagnostic questions after encrypting to said medical user interface; and said encryption device associated with said user interface decrypting the sequences of examination steps.

16. A system of claim 15 wherein after the step of associating the examination steps, said server:

determines an economic combination of the examination steps that answer said at least one or more diagnostic questions;

optimizes a sequence of the examination steps; and sends said optimized sequence of examination steps to said medical user.

17. A system of claim 16 wherein said server generates attributes for association of examination steps with said diagnostic questions, and said attributes are used for determining said economic combination of the examination steps that answer said at least one or more diagnostic questions.

18. A system of claim 15 including the further step of after optimizing the sequence of the examination steps, said server harmonizes the examination steps.

19. A system of claim 15 including providing a business logic of said medical user to said clinical knowledge server for determining kinds of information exchange between said user and said provider.

20. A system of claim 19 wherein said business logic of the user is sent to the server at the time that the diagnostic questions are sent.

21. A system of claim 15 wherein a business logic component associated with said server makes use of system utilization data from customers of the provider.

22. A system of claim 21 wherein the clinical knowledge server also has a decision support system associated therewith, and the server processes the system utilization data for extracting information about best protocols or best processing tools used for answering certain of said diagnostic questions.

23. A system of claim 15 wherein said server also requests clinical knowledge from said clinical user and said medical user and receives responsive clinical knowledge from said user.

24. A system of claim 15 wherein a business logic associated with said clinical knowledge server provides information allowing for a clinical knowledge exchange between said medical user and said provider.

* * * * *